(12) United States Patent
Laurent et al.

(10) Patent No.: US 8,001,852 B2
(45) Date of Patent: Aug. 23, 2011

(54) METHOD FOR DETECTING A RUPTURE INSIDE A STRUCTURE AND SYSTEM FOR IMPLEMENTING SAID METHOD

(75) Inventors: Eric Laurent, Charenton (FR); Bernard Basile, Plaisir (FR)

(73) Assignee: Freyssinet, Velizy Cedex (FR)

( * ) Notice: Subject to any disclaimer, the term of this patent is extended or adjusted under 35 U.S.C. 154(b) by 154 days.

(21) Appl. No.: 11/908,871

(22) PCT Filed: Mar. 15, 2006

(86) PCT No.: PCT/FR2006/000579
§ 371 (c)(1),
(2), (4) Date: Sep. 17, 2007

(87) PCT Pub. No.: WO2006/097632
PCT Pub. Date: Sep. 21, 2006

(65) Prior Publication Data
US 2008/0190217 A1    Aug. 14, 2008

(30) Foreign Application Priority Data

Mar. 17, 2005  (FR) ..................................... 05 02666

(51) Int. Cl.
*G01L 1/04* (2006.01)
(52) U.S. Cl. ................................................. 73/862.451
(58) Field of Classification Search ............. 73/862.451, 73/862
See application file for complete search history.

(56) References Cited

U.S. PATENT DOCUMENTS

| | | | | |
|---|---|---|---|---|
| 2,341,166 A * | 2/1944 | Thayer | ....................... | 114/77 R |
| 2,590,398 A * | 3/1952 | Gegenschatz | ................... | 73/828 |
| 2,593,984 A * | 4/1952 | Clary, Jr. et al. | ............. | 57/58.55 |
| 3,902,070 A * | 8/1975 | Amor et al. | .................... | 378/194 |
| 4,548,085 A * | 10/1985 | Grundy | .................... | 73/862.473 |
| 4,623,218 A * | 11/1986 | Laurette et al. | ............... | 385/101 |
| 4,633,540 A * | 1/1987 | Jungwirth et al. | ................ | 14/22 |
| 5,076,104 A * | 12/1991 | Glaesemann et al. | .......... | 73/830 |
| 5,083,469 A | 1/1992 | Percheron et al. | | |
| 5,461,743 A | 10/1995 | Stubler et al. | | |
| 5,809,710 A | 9/1998 | Jungwirth et al. | | |
| 6,142,023 A | 11/2000 | Cole et al. | | |
| 6,178,823 B1 * | 1/2001 | Sykes | ............................. | 73/827 |
| 6,239,362 B1 * | 5/2001 | Nannini | .................... | 174/40 TD |
| 6,312,635 B1 * | 11/2001 | Wang et al. | .................... | 264/235 |
| 6,343,515 B1 | 2/2002 | Dodson | | |
| 6,715,176 B2 * | 4/2004 | Stubler et al. | ..................... | 14/22 |
| 6,815,948 B1 * | 11/2004 | Kwun et al. | .................. | 324/238 |

(Continued)

FOREIGN PATENT DOCUMENTS

EP          1061204          12/2000

(Continued)

*Primary Examiner* — Lisa Caputo
*Assistant Examiner* — Octavia Davis
(74) *Attorney, Agent, or Firm* — Banner & Witcoff, Ltd

(57) ABSTRACT

The invention concerns a system for detecting a rupture inside a portion (6; 12; 13; 15) at least of one structure, delimited by a first (7; 16) and a second (7; 17) reference points of the structure, said portion having a predetermined stiffness in the absence of rupture and being subjected to a tensile or compressive stress (F). The method includes the following steps: detecting at least one length variation inside the portion of the structure, in response to a variation (?F) of the tensile or compressive stress applied to said portion; deducing from the detected variation length, the existence or not of a rupture inside said portion of the structure.

21 Claims, 7 Drawing Sheets

U.S. PATENT DOCUMENTS

| | | | |
|---|---|---|---|
| 6,901,818 B1 * | 6/2005 | Cheung | 73/862.393 |
| 6,944,550 B2 * | 9/2005 | Marchetti | 702/42 |
| 6,972,687 B1 * | 12/2005 | Marshall et al. | 340/686.1 |
| 7,181,890 B2 * | 2/2007 | Nuetzel | 52/223.13 |
| 2004/0094651 A1 | 5/2004 | Marchetti | |
| 2005/0055974 A1 | 3/2005 | Lecinq et al. | |

FOREIGN PATENT DOCUMENTS

| | | |
|---|---|---|
| EP | 1061204 A | 12/2000 |
| FR | 2652866 A | 4/1991 |
| FR | 2702782 A | 9/1994 |
| FR | 2813907 A | 3/2002 |
| FR | 2858987 A | 2/2005 |

* cited by examiner

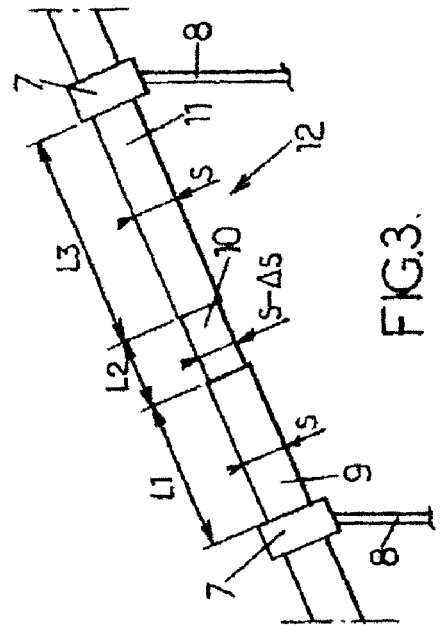
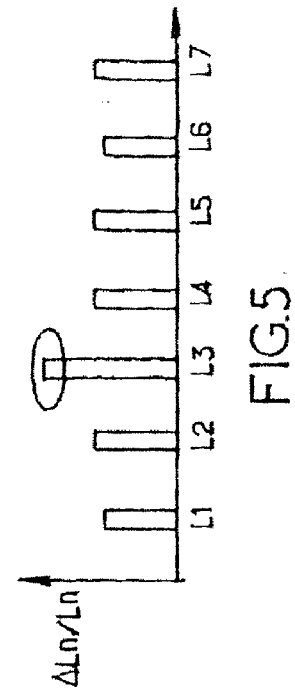
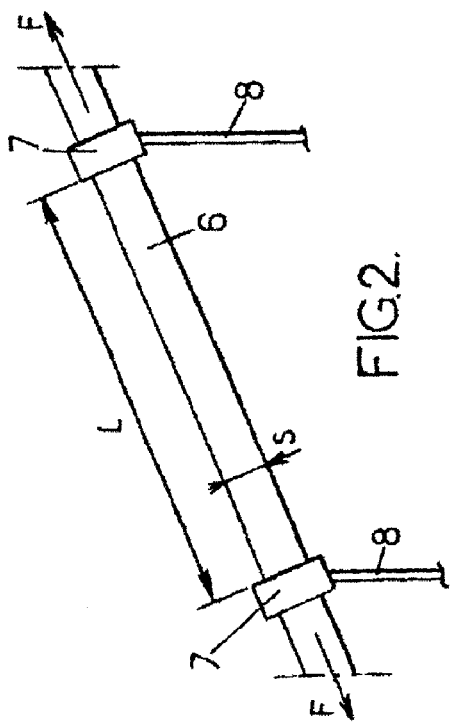
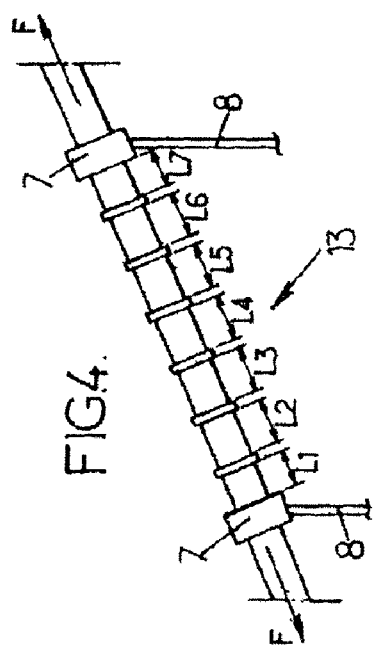

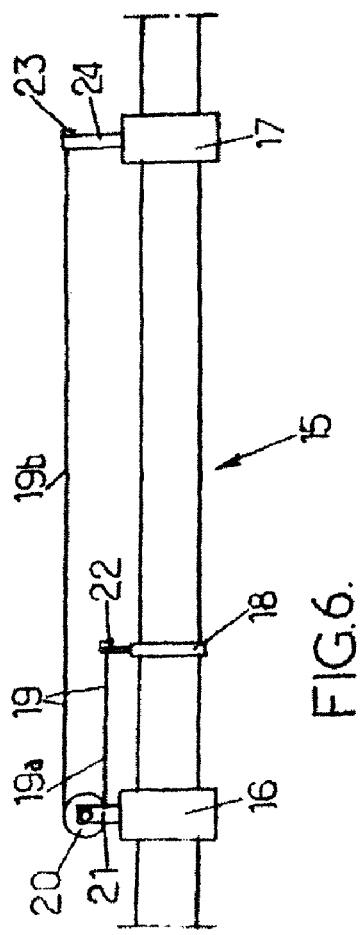
FIG.6.
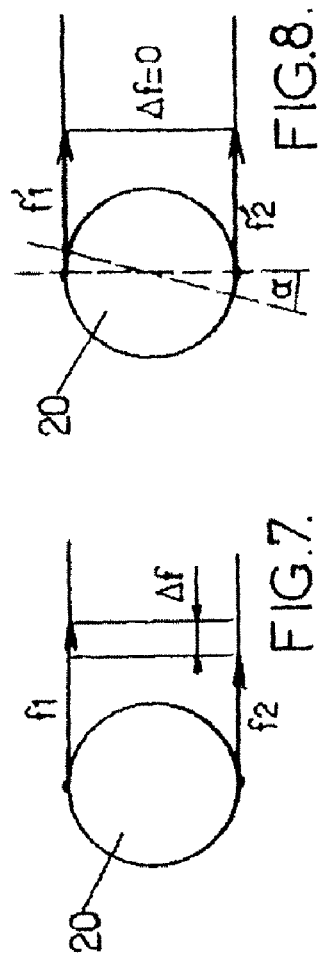
FIG.7.
FIG.8.
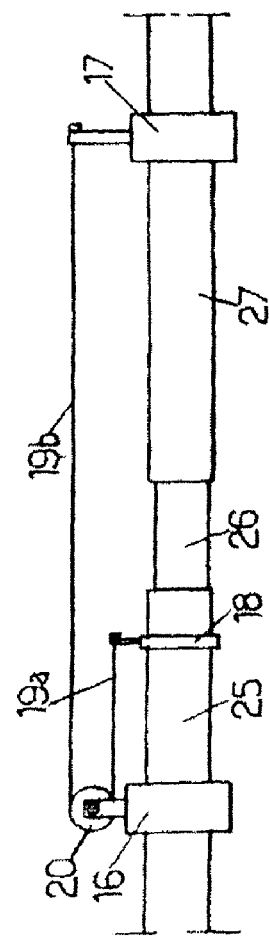
FIG.9.

METHOD FOR DETECTING A RUPTURE INSIDE A STRUCTURE AND SYSTEM FOR IMPLEMENTING SAID METHOD

BACKGROUND OF THE INVENTION

The present invention relates to the detection of breaks within a structure.

It applies particularly, although not exclusively, to the detection of breaks within a cable, such as a suspension bridge main suspension cable.

The main parts of a suspension bridge are recalled schematically in FIG. 1. This shows a suspension bridge comprising a deck 1 providing continuity of the carried way and the distribution of the forces. Hanger cables 2 support the deck and transmit the forces to the main suspension cables 3 to which they are securely attached by hanger cable collars. The main cables 3, which adopt a parabolic appearance, provide the support function. The forces can be broken down into a vertical reaction absorbed by the towers 5, and a tensile force transmitted by an anchor cable 4 securely attached to an anchor.

The integrity of a construction such as this relies in the ability of the main cables 3, of the hanger cables 2 and of the anchors to withstand the stresses resulting from the transfer of force, over an extended period of time.

These elements are thus the weak points of suspension bridges. Safety and endurance are therefore generally ensured by adopting suitable safety factors, especially as there is no redundant load path in such constructions.

The main suspension cables 3 usually consist of metal strands, generally made of steel, which are substantially parallel (although the strands are sometimes twisted). These strands are protected against corrosion by various means: heat treatment, chemical treatment, the application of paint, sheathing, etc.

However, it is impossible to rule out entirely the possibility of some of the strands that make up such main suspension cables breaking as a result, for example, of oxidation. This phenomenon is insidious because it mainly affects the internal strands around which water may infiltrate and stagnate without being eliminated by evaporation and without being immediately visible.

The substantially parallel configuration of the metal strands of the main suspension cables means that these strands rub together to a certain extent, thus limiting the extent to which any strand or strands that has or have broken retreat(s) away from a region surrounding the break point.

There then occurs what is known as re-anchorage, that is to say that, beyond this zone, the broken strands continue to contribute to the transmission of force and find themselves once again under stress. Only the break zone has a cross section that is reduced by the cross section of the broken strands and therefore a higher stress is exerted on the remaining strands in this zone. This may cause the remaining strands in the breakage zone to break if the permissible stress is exceeded. If the cause of the breakage of the initial strand or strands is still present in this zone, then this risk becomes more of a reality.

For these reasons, it is therefore important to have reliable and early detection of any break that may have occurred within such a cable, or within any other structure subjected to possible tensile or compressive forces.

It is known practice to detect the onset of breakage within a cable using an acoustic examination of the cable. The energy released as a constituent strand of the cable breaks is thus picked up and recorded using a microphone. However, this technique is able to detect breakage only at the instant at which it occurs. It does not directly provide the history of the number of breaks nor does it give any deterministic indication as to the condition of the cable. Neither is it able to characterize the breaks that have occurred directly, particularly in terms of their location and their extent.

It is a first object of the present invention to alleviate the disadvantages of the known art.

One object of the invention is more specifically to detect breaks that may have occurred within a structure such as a cable.

Another object of the invention is to characterize the breaks, particularly in terms of their location and extent.

SUMMARY OF THE INVENTION

The invention thus proposes a method for detecting a break within at least a portion of a structure, this portion being delimited by a first and a second point of reference of the structure, said portion having a predetermined stiffness in the absence of break and it being subjected to a tensile or compressive force. The method comprises the following steps:
  detecting at least one variation in length within the portion of the structure, in response to a variation in the tensile or compressive force applied to said portion;
  deducing whether or not there is a break within said portion of the structure from the detected variation in length.

This method thus makes it possible to detect any possible breaks that might be within the structure.

The following embodiments are also provided for within the scope of the present invention, alone or in any feasible combination:
  the variation in the tensile or compressive force applied to said portion is predetermined, and the deduction as to whether or not there is a break within the portion of the structure is made also on the basis of the predetermined stiffness of said portion and of said predetermined variation in the tensile or compressive force applied to said portion;
  at least two zones are defined in the length of the portion of the structure; a variation in length is detected relative to at least some of said zones, and whether or not there is a break within at least some of said zones is deduced from the detected variations in length. Any break or breaks that may have occurred within the structure can thus be located with a certain degree of accuracy;
  respective wires are stretched, one of them between one end of each of said zones and a respective rotary element connected to the first point of reference of the portion of the structure, and the other of them between said rotary element and the second point of reference of the portion of the structure, and the variation in length relative to at least some of said zones is detected from a rotation performed by said respective rotary element in response to the variation in the tensile or compressive force applied to the portion of the structure;
  the rotary element connected to the first point of reference of the portion of the structure comprises a pulley over which the respective wire passes;
  the rotation performed by the pulley is detected using a rotary sensor attached to the pulley rotation axle;
  the rotation performed by the pulley is detected using a linear displacement transducer coupled to the pulley;
  the rotation performed by the pulley is detected using the linear displacement transducer collaborating with a lever arm extending across a diameter of the pulley;

a force measurement device is coupled to the rotation axle of the pulley and is designed to measure a displacement of the respective wire, and the variation in length relative to at least some of said zones is also detected from said measurement of the displacement of the respective wire;

the rotary element connected to the first point of reference of said portion of the structure comprises a rotary arm to the ends of which strands of the respective wire are respectively connected;

a force sensor is associated with each wire to measure a force exerted on the wire on each side of the respective rotary element, and the variation in length relative to at least some of said zones is also detected from measurements of the force exerted on the respective wire;

a wire is stretched between the first and second points of reference of the portion of the structure in the form of a network of a number of rotary elements which are alternately connected to the first point of reference of the portion of the structure and to one end of each of said zones;

the variation in length relative to at least some of said zones is detected from a rotation performed by at least one respective rotary element of said network in response to the variation in the tensile or compressive force applied to the portion of the structure;

said wire is connected to two points of the first point of reference of the portion of the structure;

the variation in the tensile or compressive force applied to said portion is predetermined, and a proportion of the cross section of said portion of the structure that has experienced a break is also deduced from said predetermined variation in the tensile or compressive force applied to said portion and from the detected variations in length, at least in some of said zones;

the variation in the tensile or compressive force applied to the portion of the structure is progressive and at least some of the steps of the method are repeated at several instants during this progression;

further zones are then defined in the length of the portion of the structure, which are more concentrated around the zones in which a break has already been detected, and at least some of the steps of the method are repeated relative to said further zones;

said structure is a cable comprising a plurality of substantially parallel metal strands;

said structure is a main suspension cable of the suspension bridge and said first and second reference points delimiting the portion of the cable are situated at the hanger cable collars;

the variation in the tensile or compressive force applied to the portion of the cable is obtained by loading the suspension bridge using a reference convoy.

The present invention also proposes a system designed to implement the aforementioned method. This system comprises means for detecting at least one variation in length within at least a portion of a structure, this portion being delimited by a first and a second point of reference of the structure and having a predetermined stiffness in the absence of breakage, in response to a variation in a tensile or compressive force applied to said portion, the variation in length detected by the detection means providing an indication as to whether or not there is a break within said portion of the structure.

BRIEF DESCRIPTION OF THE DRAWINGS

FIG. 2 depicts a portion of a "sound" cable;

FIG. 3 depicts a portion of a cable that has experienced a break;

FIG. 4 depicts a portion of a cable along the length of which a plurality of zones have been defined;

FIG. 5 is a graph showing variations in length for each of the zones of the cable portion of FIG. 4;

FIG. 6 depicts a system for detecting a break according to one embodiment of the invention;

FIGS. 7 and 8 show an operating principle of the system of FIG. 6;

FIG. 9 depicts a system for detecting a break according to the invention, applied to a portion of a cable that has experienced a break;

DESCRIPTION OF PREFERRED EMBODIMENTS

FIG. 2 shows a length or portion 6 of cable to which the system and method according to the invention may be applied, it being understood that the invention may be applied to any kind of structure that has a predetermined stiffness, such as a girder, a slab, etc.

Figure 1:
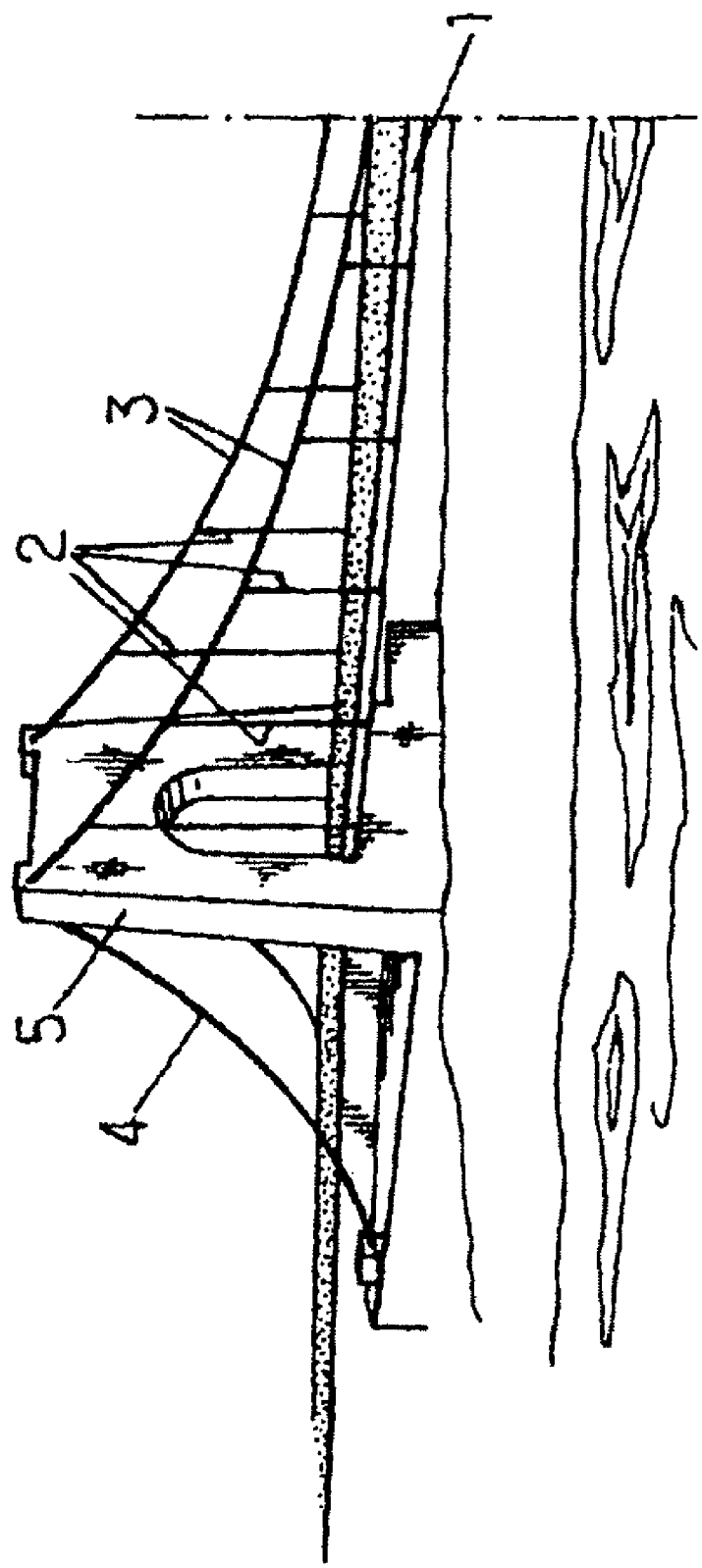
FIG. 1, on which comment has already been passed, is a simplified diagram of a suspension bridge.

The cable of FIG. 1 is, for example, a suspension bridge main suspension cable consisting of substantially parallel (possibly twisted) metal strands. The portion 6 thus extends between two hanger cable collars 7 to which the hanger cables 8 are securely attached. It has a length L, a cross section S and an elastic modulus E. When the constituent strands of the cable are made of steel, the elastic modulus E is that of steel. It is therefore possible to calculate the stiffness K of the portion 6, as if it were a spring, that is to say using:

$$K = E \times S/L \qquad (1)$$

The portion 6 of cable is normally subject to a force F. When a variation in force $\Delta F$ arises in the cable, it therefore causes a variation in length $\Delta L$ of the portion 6 that is proportional to $\Delta F$ and inversely proportional to the stiffness K, namely:

$$\Delta L = \Delta F/K \qquad (2)$$

When one or more strands of the cable is or are broken within the portion 6, this portion experiences a reduction in its cross section by the cross section corresponding to that of the broken strands, namely ΔS, in a zone surrounding the break point. As explained above, this break point is limited by internal friction between the strands. The portion can therefore be considered to behave like a plurality of springs in series, each one having a stiffness dependent on its cross section.

FIG. 3 illustrates this model. It shows a portion 12 of cable extending between two hanger cable collars 7.

The overall length L of this portion is split between three successive zones 9 to 11 of respective lengths L1, L2 and L3. The zone 10 is a break zone, that is to say the zone in which the strands of the cable have broken, which means that the cross section of the portion 12 is S−ΔS in this zone, as compared with S in the zones 9 and 11 not affected by the break.

According to formula (1), the stiffnesses in zones 9 to 11 are, respectively:

$$K1 = E \times S/L1$$

$$K2 = E \times (S-\Delta S)/L2$$

$$K3 = E \times S/L3 \quad (3)$$

The total stiffness K' of the portion 12 can therefore be written as a combination of these springs in series, giving:

$$1/K' = 1/K1 + 1/K2 + 1/K3 \quad (4)$$

This stiffness K' is lower than that of an "sound" portion, that is to say one that does not have any break within it, such as the portion 6 in FIG. 2.

As a result, an increase in the force in this portion 12 causes an elongation that is greater than it would be without this localized loss of cross section. This extra elongation is proportional to the increase in force and to the length of the portion affected by this loss.

Thus, detecting the increase in length ΔL' of the portion 12 when subjected to an extra force ΔF may make it possible to conclude that there is a break within this portion. Knowing the value of the extra force ΔF and of the stiffness K of the portion when there is no break, makes it possible to verify that the elongation ΔL' is greater than that ΔL of a sound portion, and therefore from this to deduce that there is a break within the portion 12.

Although operation such as this enables a break to be detected within a portion of a cable, this detection may be considered to be insufficiently early in true-life applications, because the additional variation in the length of the portion becomes significant only when the cross section lost is relatively great, and so too the length of the break zone. The accuracy with which the variation in length of the portion is measured may be the limiting factor in this case.

FIG. 4 shows a portion 13 of cable along which a series of differential measurements is made, so as to obtain a better detection of breakage than was obtained in the previous case.

This portion 13 is divided into seven zones of respective lengths L1 to L7. It is subjected to an initial tensile force F. As in the previous case, the force F can be increased by a value ΔF and a resulting variation in length detected for the various zones of the portion 13.

FIG. 5 shows an example of values of the variation in length obtained for each of the seven zones of the portion 13. The variations in length are advantageously expressed in relative terms, that is to say using the expression ΔLn/Ln, where n ranges from 1 to 7. It can be seen from FIG. 5 that the variation in length obtained for the length zone 3 of the portion 13 has the highest value. In accordance with that which was explained above, that means that the stiffness in this zone is lower than the stiffness in the other zones, which indicates a reduction in cross section as a result of a break in this zone.

As an alternative, rather than comparing the variations in length of all the defined zones directly against one another, the variation in length of each zone could be compared with the overall variation in length of the portion considered. It is then possible to determine what contribution each zones makes to the variation in length of the portion and from this to deduce whether or not there is a break in each of the zones considered.

This embodiment of the invention thus makes it possible to reach a conclusion as to the possible presence of breaks within a portion of cable. It also allows any breaks that might be present to be located with a certain degree of precision dependant on the number of zones defined along the length of the portion. Finally, comparing certain detected variations in length may, to a certain extent, make it possible to get around the problem of the precision of the measurement as mentioned in the context of the previous embodiment.

Another embodiment of the invention which further improves the reliability with which breaks can be detected and, if present, characterized, will be described hereinbelow.

FIG. 6 shows, straightened out to make it easier to understand, a portion 15 of cable delimited by points of reference which may, for example, be hanger cable collars 16 and 17, in the case of a suspension bridge main suspension cable.

A pulley 20 is mounted rigidly on the hanger cable collar 16 via a rod 21. This rod is preferably very rigid so that all the movements of the collar 16 are transferred in full to the pulley.

A wire 19 of constant cross section is anchored at its end 22 on an intermediate collar 18 and at its end 23 on the hanger cable collar 17 using a rod 24. This rod 24 is also preferably very rigid so that any tensile force applied to the wire does not deform it. The wire 19 passes over the pulley 20 which can turn about its axle borne by the rod 21. The wire 19 is, for example, stretched using devices situated at its ends 22 and 23 or alternatively by an antibacklash means belonging to the pulley 20. There is no significant backlash between the pulley and its axle.

Thus, the wire 19, of predetermined elasticity, is stretched partially over a zone of the portion 15 that extends between the intermediate collar 18 and the pulley 20 (strand 19a) and partly over the entire length of the portion 15, that is to say between the pulley 20 and the hanger cable collar 17 (strand 19b).

As explained above, when the cable of FIG. 6 is subjected to an additional force ΔF, this causes a proportionate variation in length between the collars 16 and 17. This elongation is passed on to the strand 19b of the wire which reacts to it by exerting a tensile force on the pulley 20 that has a tendency to cause the pulley to turn. In the example illustrated in FIG. 6, the pulley therefore has a tendency to turn in the clockwise direction when the additional force ΔF exerted on the cable is a tensile force.

However, since the collar 18 is firmly attached to the cable, it is liable to experience movement due to the elongation of the cable. This movement is dependent on its position within the portion 15. Because the strand 19a of the wire is connected to the intermediate collar 18, it experiences an identical elongation which in reaction causes a tensile force to be exerted on the pulley 20 that tends to make the pulley turn in the opposite direction. In the example illustrated in FIG. 6, the pulley therefore tends to turn in the anticlockwise direction when the additional force ΔF exerted on the cable is a tensile force.

The elastic modulus of the wire 19 is denoted Ef and its cross section is denoted s. l1 denotes the length of the strand 19b and l2 denotes the length of the strand 19a. Δl1 denotes the elongation of the strand 19b as a result of the relative movement of the collars 16 and 17. Δl2 denotes the elongation of the strand 19a as a result of the relative movement of the collars 16 and 18.

Because the elongations experienced by the strands of the wire are preferably transmitted in full by the collars to which they are attached, they are identical to those of the cable.

If f1 denotes the force resulting from the elongation Δl1 of the strand 19b and f2 denotes the force resulting from the elongation Δl2 of the strand 19a, then the following equations can be written:

$$f1 = Ef \times s/l1 \times \Delta l1, \text{ or alternatively } f1 = Ef \times s \times \Delta l1/l1, \text{ and}$$

$$f2 = Ef \times s/l2 \times \Delta l2, \text{ or alternatively } f2 = Ef \times s \times \Delta l2/l2 \quad (5)$$

The force differential between f1 and f2 causes the pulley 20 to rotate until these forces reach equilibrium, because this rotation in turn causes a change in length of the strands 19a and 19b of the wire 19.

This phenomenon is illustrated in FIGS. 7 and 8. FIG. 7 depicts the forces f1 and f2 exerted on the strands on the wire 19 on each side of the pulley 20.

In the example depicted, the value of f1 is greater than that of f2, thus creating a differential Δf able to cause the pulley 20 to rotate in the clockwise direction.

FIG. 8 shows the same device once the forces have reached equilibrium, that is to say once the forces f'1 and f'2 exerted on the strands of the wire 19 on each side of the pulley 20 are equal, so that the pulley 20 stops turning, the force differential now becoming zero. It will be noted that the differential Δf has caused the pulley 20 to rotate through an angle α, as illustrated in FIG. 8. This angle α is proportional to the force differential Δf which is itself directly proportional to the relative elongations of the strands 19a and 19b, as shown by formulae (5).

Because the relative elongations of the strands 19a and 19b are properly transmitted by the collars of the cable to which collars they are attached, the angle α is therefore representative of the differential in relative elongation of the cable. In other words, the rotation of the pulley provides a reliable indication as to the relative variations in length of certain zones of the portion in question.

Thus, when the portion of cable is "sound", that is to say when no metal strand of the portion of cable has broken, its relative elongation is constant along its entire length if the tensile force is varied. In particular, Δl1/l1=Δl2/l2. In this case, the pulley does not turn at all because, in accordance with formulae (5), the forces f1 and f2 are identical.

FIG. 9 shows the same system for detecting a break as was shown in FIG. 6, applied to a portion of cable that has experienced a loss of cross section. This portion can be broken down into three parts 25 to 27.

The intermediate zone 26 is the zone within which the break has occurred.

In the example illustrated in FIG. 9, it will be understood from the foregoing that the strand 19b undergoes greater relative elongation than the strand 19a when the portion is subjected to an additional tensile force. This causes the pulley 20 to rotate in proportion with this imbalance. The final angle through which the pulley 20 rotates thus determines the relative elongation differential of the cable.

It will be noted that a tensile force exerted on the cable results in an elongation of the portion considered. Conversely, a compressive force may, on the other hand, result in the portion becoming shorter.

Figure 10:
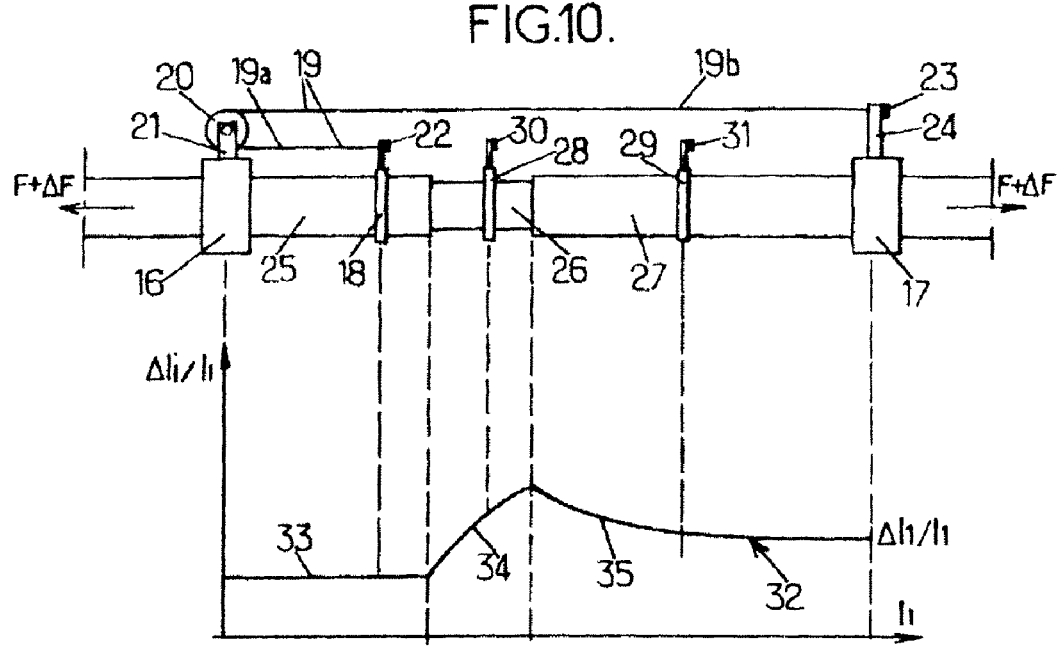
FIG. 10 depicts a system for detecting a break according to one embodiment of the invention and a graph of variations in length given by the system.

FIG. 10 shows a system for detecting a break applied to a portion of cable, similar to that of FIG. 9, but in which system several intermediate collars 18, 28 and 29 have been positioned along the length of the portion of cable, so as to obtain various measurements simultaneously or in succession.

Each intermediate collar defines a respective zone of the portion considered extending, for example, between the hanger cable collar 16 and the intermediate collar in question. Detecting any breaks that might be present will be performed relative to each of the zones thus defined.

According to that which was described above, a wire is stretched between an intermediate collar 18, 28 or 29 and the hanger cable collar 17, via the pulley 20 fixed to the suspension collar 16. The force F exerted on the cable is then increased by the value ΔF, thus causing a relative elongation of the portion.

This then yields a relative variation in length Δli/li for each of the zones defined, where li denotes the length of the zone considered between the collar 16 and the corresponding intermediate collar. In the example illustrated in FIG. 10, this then yields three length variation values each corresponding to one of the zones defined in relation to one of the intermediate collars 18, 28 or 29.

These measurements Δli/li may be plotted on a graph as depicted in FIG. 10, as a function of li. Depending on the number of zones defined along the length of the portion of cable, that is to say on the number of intermediate collars used, it is thus possible to obtain a curve of greater or lesser precision charting the variations in length of the portion along the length of this portion.

The curve 32 depicted in FIG. 10 is one example of a curve thus obtained. It shows, in a portion 33, a constant relative elongation that indicates that the geometric characteristics of the cable are unchanged in that portion and therefore that the stiffness of the corresponding part 25 of the portion is unchanged. In other words, the cross section of the part 25 of the portion of cable has not been corrupted, which indicates that no strands are broken in this zone.

A second portion 34 of the curve 32 corresponds to the part 26 of the portion of cable. This part 26 shows a change in cross section resulting from breakage of the cable, which manifests itself in an increase, for example a parabolic increase, in the curve in its portion 34. The stiffness of the part 26 of the portion of cable is actually lower than that of the part 25. The increase in the curve 32 is representative of the effect of the two parts 25 and 26 of the portion of cable of different stiffnesses placed in series.

A third portion 35 of the curve 32 corresponds to the part 27 of the portion of cable. In this portion 35, the curve 32 decreases in for example a parabolic shape. This is representative of the effect of the three parts 25 to 27 of the portion of cable placed in series and of the fact that the cross section of the cable increases between the parts 26 and 27 of the portion, the part 27 not having been affected by the break.

The right-most value of the curve 32 corresponds to the variation in length Δl1/l1 at the hanger cable collar 17.

Simulation makes it possible to check that, in a typical exemplary embodiment, and once again adopting the notations L1, L2, L3, S and ΔS used above with reference to FIG. 3, the various portions 33-35 of the curve 32 are of the following forms respectively: A, B+(A−B).L1/li and A+(B−A).L2/li, where A=ΔF/(E×S) and B=ΔF/(E×(S−ΔS)).

An analysis of the curve 32 therefore makes it possible to determine those zones of the portion of cable that have a break within them. A more detailed analysis of the curve, based in particular on values of the gradient or curvature of its various parts, also makes it possible precisely to determine the position of the break and the extent thereof. With prior knowledge of the additional force ΔF applied to the cable, it is possible to evaluate the cross section of cable lost as a result of the breakage of metal strands.

It will be noted that the curve 32 can be obtained using the break detection system described above, but that it may also be obtained using any measurement means able to determine the values Δli/li.

Figure 11:
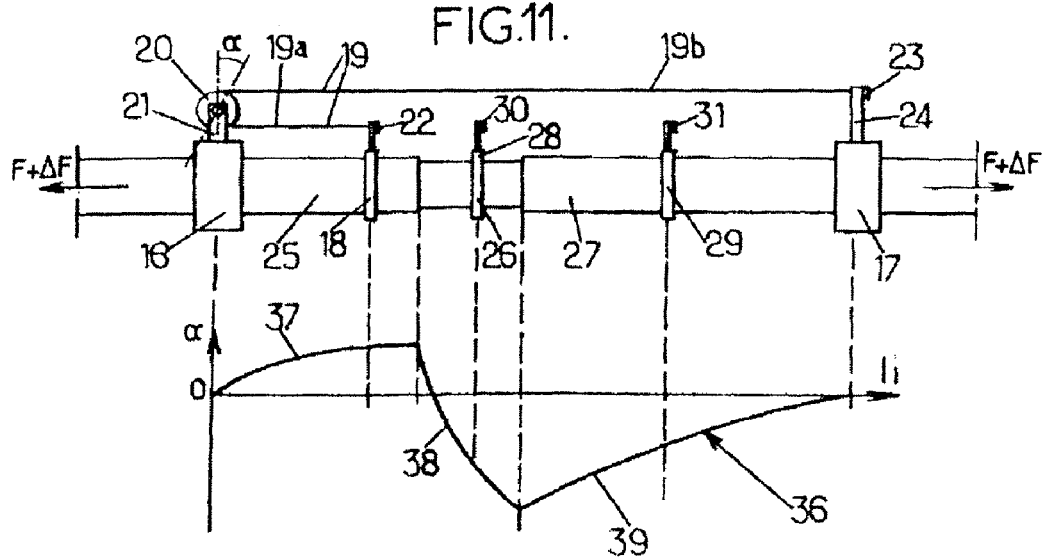
FIG. 11 depicts a system for detecting a break according to one embodiment of the invention and a graph of variations in angle given by the system.

When the break detection system used is the one described above it may be advantageous, in practice, to construct a curve representing the angle of rotation α of the pulley as a function of length li. A curve such as this is depicted in FIG. 11. It is dependent on the curve 32 depicted in FIG. 10 because of the relationship there is between the angle of rotation α of the pulley 10 and the force differential exerted on the two strands of the wire 19. In particular, we again find three portions of curve 37 to 39 with different curvatures, underlying the series-effect of successive parts of the portion of cable of different stiffnesses. In particular, the portions 37 and 39 of this curve correspond to rotations of the pulley in opposite directions.

Simulation makes it possible to check that, in a typical exemplary embodiment, and again using the notations L, L1, L2, L3, S and ΔS used above with reference to FIGS. 2 and 3, the various portions 37-39 of the curve 36 are, give or take a multiplicative factor, respectively of the following forms:

$$(L - li \cdot f1(li))/(1 + f1(li)), (L - li \cdot f2(li))/(1 + f2(li))$$

and $$(L - li \cdot f3(li))/(1 + f3(li)),$$

where $$f1(li) = \frac{L}{li} + \frac{(B-A) \cdot L2}{(A+1) \cdot li}, F2(li) = \frac{(A+1) \cdot L + (B-A) \cdot L2}{(B+1) \cdot li + (A-B) \cdot L1}$$

$$f3(li) = \frac{(A+1) \cdot L + (B-A) \cdot L2}{(A+1) \cdot li + (B-A) \cdot L2}$$

and where A=ΔF/(E×S) and B=ΔF/(E×(S−ΔS)). The multiplicative factor is the inverse of the radius of the pulley 10. Thus, the smaller the radius of the pulley, the greater the sensitivity with which the angle α through which this pulley rotates can be measured.

The benefit of a curve of the type of curve 36 is that it can be plotted directly as the pulley rotation angle values are recorded, without additional calculation. Analysis of such a curve 36 can be performed in a similar way to analysis of the curve 32 described above. In particular, it makes it possible to reveal a zone of smaller cross section within the portion of cable considered and to assess the extent thereof. Analysis of the portions of this curve also allows the proportion of the cross section that has been lost to be determined, if the additional force applied to the cable is known.

A system such as this is also able to detect a number of changes in cross section along the portion, which then appear as a corresponding number of changes in gradient or curvature in the curves obtained.

In order for the data obtained to be fully exploitable, it is desirable for the additional force applied to the cable to be predetermined. One simple way of achieving this is, for example, to load up the construction of which the cable forms part, such as a suspension bridge, with a reference convoy the characteristics of which are known, having previously calculated the additional force in the portions of cable that result from the presence of this convoy. An operation such as this does not generally impose any constraint other than the temporary closing of the construction to traffic.

Figure 12:
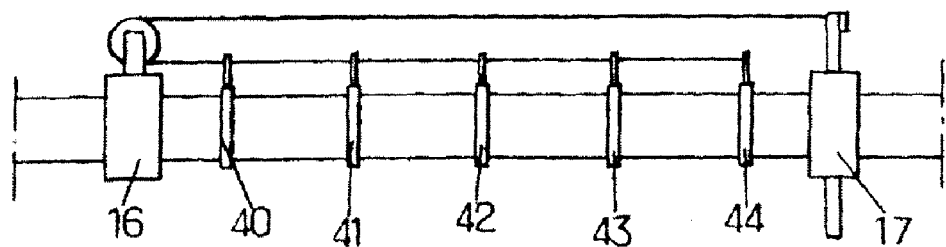
FIG. 12 depicts a system for detecting a break according to one embodiment of the invention.
Figure 13:
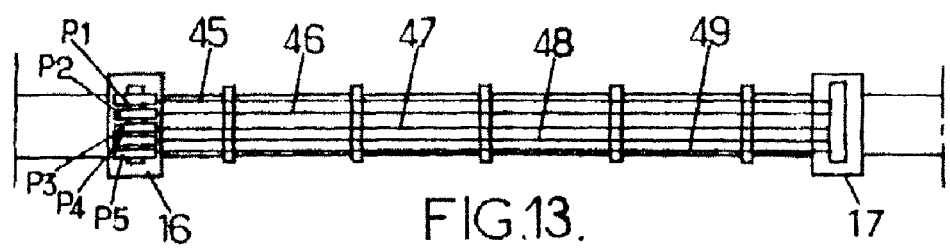
FIG. 13 depicts the detection system of FIG. 12, in a view from above.

FIGS. 12 and 13 show, in a side view and in a view from above, respectively, a system for detecting breaks according to the invention as described above, in which system a number of intermediate collars 40-44 are positioned along the portion of cable considered, between the end collars 16 and 17. Wires 45-49 are stretched respectively from each of these collars to a corresponding pulley P1-P5 fixed to the collar 16, and then as far as the opposite collar 17. This set up allows length variation (or pulley rotation angle) values to be obtained simultaneously for each of the zones of the portion delimited by an intermediate collar. In this case, the construction need be loaded up by a reference convoy only once in order to obtain all the required data.

The wires such as the wires 19 and 45-49 in the figures commented on above may advantageously be pretensioned to a sufficient tension that the additional force exerted on the cable is immediately converted into an elongation of the strands. The measurement is sensitive right from the very onset of the phenomenon, as all "slack" is eliminated.

A force measurement device may be associated with the axle of each pulley and this would make it possible, on the one hand, to ensure that the wires were pretensioned, and, on the other hand, to make elongation measurements, the characteristics of the wires used being fully known.

It is also possible to add a force sensor to each of the strands on their tensioning device (at the points 22 and 23 in FIG. 6 for example) or elsewhere, in order to corroborate the pulley rotation angle measurement. This then improves the reliability with which breaks can be detected.

The rotation of the pulley may advantageously be measured using a rotary sensor firmly attached to the pulley axle. As an alternative, this measurement may be transferred to a linear displacement transducer the sensitivity of which can be increased using a lever arm. This last embodiment is illustrated in FIGS. 14 and 15.

Figure 14:
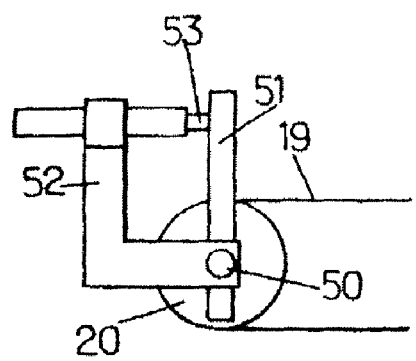
FIGS. 14 and 15 depict an angle measuring module used according to one embodiment of the invention.
Figure 15:
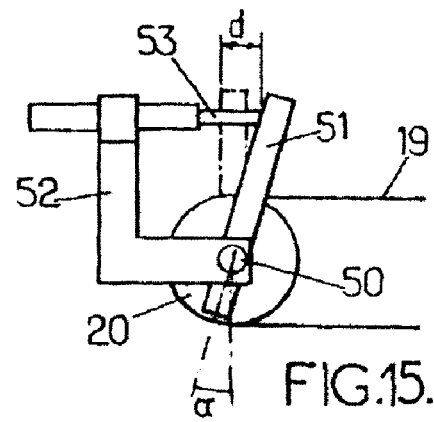

FIG. 14 thus shows a linear displacement transducer 52 mounted on the rotation axle 50 of the pulley 20. This sensor is equipped with a moving finger 53 of linear travel that bears against a lever arm 51 fixed to the pulley along the diameter thereof. Before the extra force is exerted on the cable (not depicted) bearing the break detection system, the pulley 20 of the example depicted in FIG. 14 is in an initial position such that the lever arm 51 is vertical.

When an extra force is exerted on the cable, the movement of the wire 19 causes the pulley 20 to rotate, for example in the clockwise direction, through an angle α. The lever arm 51 therefore moves with the pulley in such a way that the finger 53 extends by a corresponding length d in order to remain in contact with the lever arm. This length d can be used to determine a relative variation in length at a zone of the portion of cable considered, in place or in addition to the measuring of the angle α.

Figure 16:
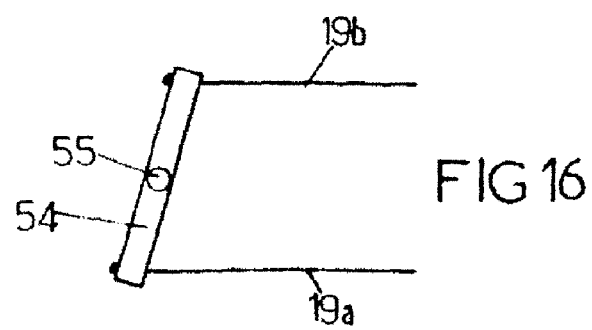
FIG. 16 depicts a rotary element used in one embodiment of the invention.

FIG. 16 shows a rotary element that can be used in place of or in addition to the pulley 20. It is an arm 54 able to rotate about an axle 55. In this embodiment, the strands 19a and 19b of the wire used in the break detection system are each connected to one of the ends of the arm 54 so as to cause the arm to rotate about its axle as a function of the force exerted on each of these arms, under the effect of the elongation of the corresponding zones of the cable.

In one advantageous embodiment of the invention, use may be made of the progressive increase of the additional force ΔF applied to the cable, for example by the loading-up of the construction of which it forms part using a reference convoy. The variations in length of certain zones of the portion of cable considered (or alternatively the corresponding angle measurements) are then obtained at various stages in the loading operation.

Figure 17:
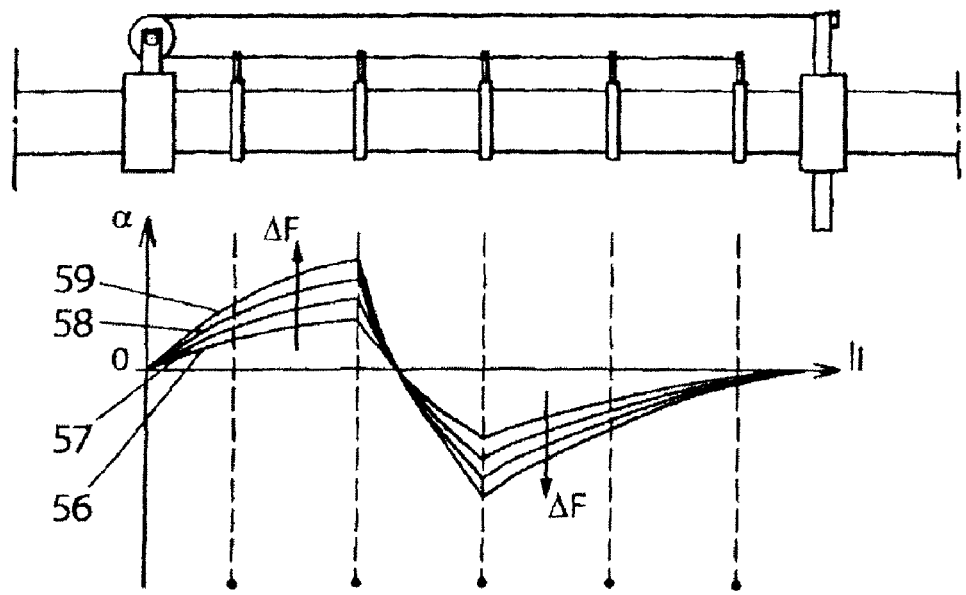
FIG. 17 depicts a system for detecting a break and a plurality of graphs of variations in angle given by the system according to one embodiment of the invention.

This embodiment is illustrated in FIG. 17 where it can be seen that measurement points are obtained at successive instants, so that curves 56-59 can be plotted as the additional force ΔF progresses. Obtaining these various curves provides an amount of data able to make the analysis of the phenomenon, and therefore detection of any breaks there might be within the cable, even more reliable. Advantageously, attempts may be made to obtain measurements continuously during the force increase phase. Other data such as the position of the convoy, the temperature, etc., may also be obtained using sensors in order better to monitor and analyze the measurements.

Figure 18:
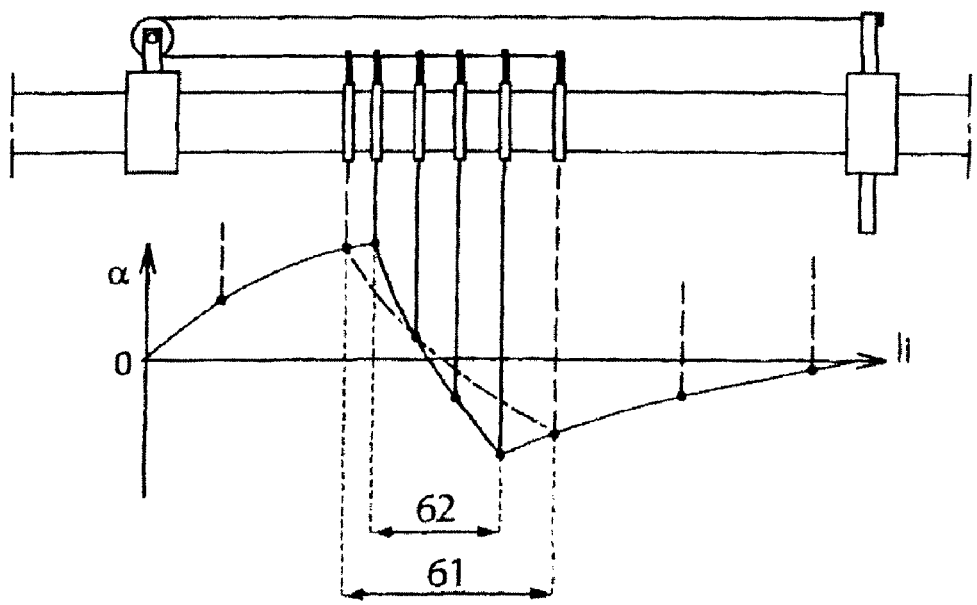
FIG. 18 depicts a system for detecting a break and a plurality of graphs of variations in angle given by the system according to one embodiment of the invention.

FIG. 18 shows another advantageous embodiment of the invention in which a first curve of angle α or any other parameter representative of the variation in length of a zone of the portion of the cable considered is first of all obtained, for example using the break detection system of FIG. 17. Next, having detected a break in a particular zone of the portion of the cable (the zone corresponding to the portion 61 of the first curve of FIG. 18), the break detection system is removed and re-fitted in such a way that it allows measurements to be taken in a more concentrated area around the detected break zone.

To do this, the intermediate collars are repositioned closer together around the detected break zone. This then provides further angle α values so that the first curve obtained can be refined in the relevant zone. It can thus be seen, in the example illustrated in FIG. 18, that the refined curve has a portion 62 with a particularly notable decrease, indicating that a break has occurred in the corresponding zone of the cable.

Of course, other alternative forms may be derived from the general principles explained hereinabove and also form part of the present invention. In particular, other relevant parameters, in addition to or in place of the parameters Δli/li and α defined above may be used to detect variations in length within the cable in response to a variation in the tensile or compressive force applied to it. If necessary, it may then be possible to anticipate adapting the break detection system in order to measure such parameters.

Figure 19:
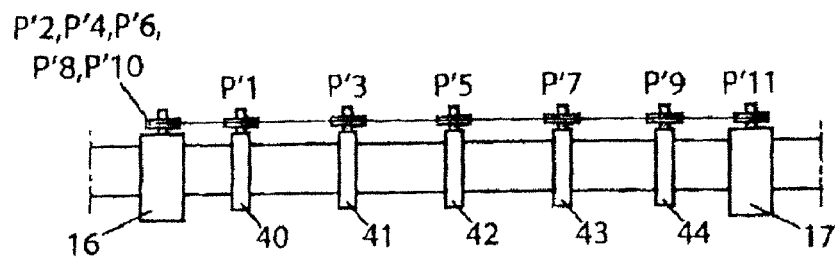
FIG. 19 depicts a system for detecting a break according to one embodiment of the invention.
Figure 20:
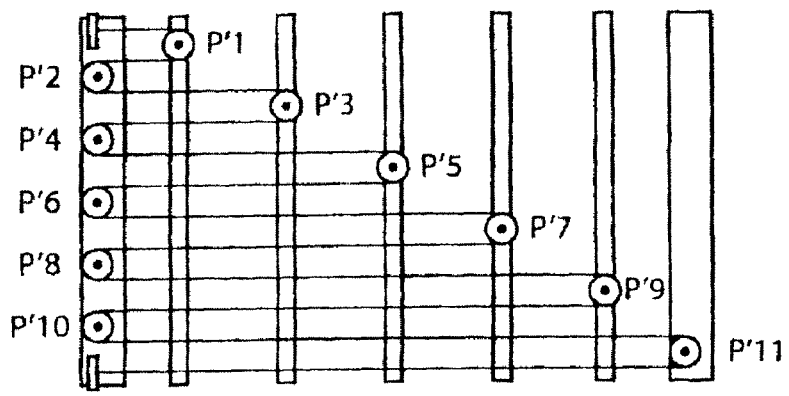
FIG. 20 depicts the detection system of FIG. 19 in a view from above.

FIGS. 19 and 20 show another example of a system according to another advantageous embodiment of the invention. Unlike the systems depicted with reference to FIGS. 12 and 13, this system has just one wire, which runs between a network of a plurality of rotary elements such as pulleys P'1 to P'11.

Figure 21:
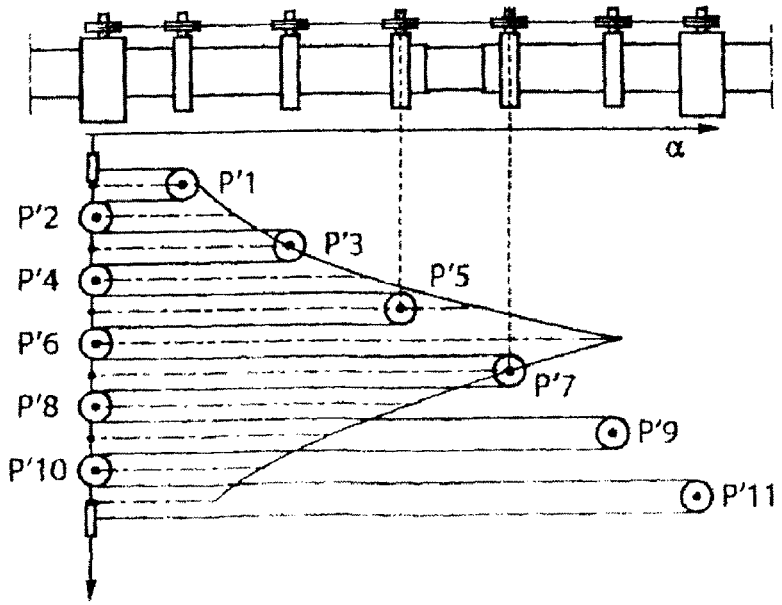
FIG. 21 depicts a system for detecting a break and a plurality of graphs of variations in angle given by the system according to one embodiment of the invention.

FIG. 21 shows a system similar to that of FIGS. 19 and 20, mounted on a cable which has a break within it. During the loading test, the Δli/li discrepancies become amplified. A variation curve can then be plotted according to the principles explained above. When this curve shows a variation in the rotation angle α of at least some of the pulleys used (for example each of the pulleys P'1, P'3, P'5, P'7, P'9 and P'11 in order to obtain a measurement for each zone of the cable), it is then possible to detect from this a significant change in sign of gradient or curvature at the smaller cross section.

This change in sign of gradient or of curvature is advantageous, because it allows a particularly clear-cut detection of the break zone, as compared with a simple change in gradient or change in curvature, for example.

Other systems are of course also conceivable within the scope of the present invention.

The invention claimed is:

1. A method for detecting a break within at least a portion of a structure, said structure being a cable comprising a plurality of substantially parallel metal strands, this portion being delimited by a first and a second point of reference of the structure, said portion having a predetermined stiffness in the absence of break and it being subjected to a tensile or compressive force, the method comprising:
   detecting at least one variation in length within the portion of the structure, in response to a variation in the tensile or compressive force applied to said portion;
   detecting a potential break of at least one but not all of the substantially parallel metal strands of said plurality within said portion of the structure depending on a value and/or a behavior of the detected variation in length.

2. The method as claimed in claim 1, in which the variation in the tensile or compressive force applied to said portion is predetermined, and in which the detection of a potential break within the portion of the structure is made also depending on the predetermined stiffness of said portion and of said predetermined variation in the tensile or compressive force applied to said portion.

3. The method as claimed in claim 1, in which at least two zones are defined in the length of the portion of the structure, in which a variation in length is detected relative to at least some of said zones, and in which a potential break within at least some of said zones is detected depending on a value and/or a behavior of the detected variations in length.

4. The method as claimed in claim 3, in which a respective wire is stretched, on the one hand between one end of each of said zones and a respective rotary element connected to the first point of reference of the portion of the structure, and on the other hand between said rotary element and the second point of reference of the portion of the structure, and in which the variation in length relative to at least some of said zones is detected from a rotation performed by said respective rotary element in response to the variation in the tensile or compressive force applied to the portion of the structure.

5. The method as claimed in claim 4, in which the rotary element connected to the first point of reference of the portion of the structure comprises a pulley over which the respective wire passes.

6. The method as claimed in claim 5, in which the rotation performed by the pulley is detected using a rotary sensor attached to the pulley rotation axle.

7. The method as claimed in claim 5, in which the rotation performed by the pulley is detected using a linear displacement transducer coupled to the pulley.

8. The method as claimed in claim 7, in which the rotation performed by the pulley is detected using the linear displacement transducer collaborating with a lever arm extending across a diameter of the pulley.

9. The method as claimed in claim 5, in which a force measurement device is coupled to the rotation axle of the pulley and is designed to measure a displacement of the respective wire, and in which the variation in length relative to at least some of said zones is also detected from said measurement of the displacement of the respective wire.

10. The method as claimed in claim 4, in which the rotary element connected to the first point of reference of said portion of the structure comprises a rotary arm to the ends of which strands of the respective wire are respectively connected.

11. The method as claimed in claim 4, in which a force sensor is associated with each wire to measure a force exerted on the wire on each side of the respective rotary element, and in which the variation in length relative to at least some of said zones is also detected from measurements of the force exerted on the respective wire.

12. The method as claimed in claim 3, in which a wire is stretched between the first and second points of reference of the portion of the structure in the form of a network of a number of rotary elements which are alternately connected to the first point of reference of the portion of the structure and to one end of each of said zones, and in which the variation in length relative to at least some of said zones is detected from a rotation performed by at least one respective rotary element of said network in response to the variation in the tensile or compressive force applied to the portion of the structure.

13. The method as claimed in claim 12, in which said wire is connected to two points of the first point of reference of the portion of the structure.

14. The method as claimed in claim 3, in which the variation in the tensile or compressive force applied to said portion is predetermined, and in which a proportion of the cross section of said portion of the structure that has experienced a break in at least some of said zones is also deduced from said predetermined variation in the tensile or compressive force applied to said portion and from the detected variations in length.

15. The method as claimed in claim 3, in which the variation in the tensile or compressive force applied to the portion of the structure is progressive and in which at least some of the steps of the method are repeated at several instants during this progression.

16. The method as claimed in claim 3, in which further zones are then defined in the length of the portion of the structure, which are more concentrated around the zones in which a break has already been detected, and in which at least some of the steps of the method are repeated relative to said further zones.

17. The method as claimed in claim 3, in which a respective wire is stretched, on the one hand between one end of each of said zones and the first point of reference of the portion of the structure, and on the other hand between the first point of reference of the portion of the structure and the second point of reference of the portion of the structure, and in which the variation in length relative to at least some of said zones is detected by measuring a force differential exerted in said wire.

18. The method as claimed in claim 1, in which said structure is a main suspension cable of a suspension bridge and in which said first and second reference points delimiting the portion of the cable are situated at hanger cable collars.

19. The method as claimed in claim 18, in which the variation in the tensile or compressive force applied to the portion of the cable is obtained by loading the suspension bridge using a reference convoy.

20. The method as claimed in claim 1, wherein detecting a potential break within said portion of the structure comprises detecting a local change in the value and/or the behavior of the detected variation in length within the portion of the structure.

21. A system comprising means for detecting at least one variation in length within at least a portion of a structure, said structure being a cable comprising a plurality of substantially parallel metal strands, this portion being delimited by a first and a second point of reference of the structure and having a predetermined stiffness in the absence of breakage, in response to a variation in a tensile or compressive force applied to said portion, and means for detecting a potential break of at least one but not all of the substantially parallel metal strands of said plurality within said portion of the structure depending on a value and/or a behavior of the detected variation in length.

* * * * *